(12) United States Patent
Sano et al.

(10) Patent No.: US 9,562,858 B2
(45) Date of Patent: Feb. 7, 2017

(54) FLUID CONCENTRATION MEASURING DEVICE

(71) Applicants: NIPRO CORPORATION, Osaka (JP); HARADA ELECTRONICS CO., LTD., Hokkaido (JP)

(72) Inventors: Yoshihiko Sano, Osaka (JP); Masahide Harada, Hokkaido (JP)

(73) Assignees: Nipro Corporation, Osaka (JP); Harada Electronics Co., Ltd., Hokkaido (JP)

( * ) Notice: Subject to any disclaimer, the term of this patent is extended or adjusted under 35 U.S.C. 154(b) by 0 days.

(21) Appl. No.: 14/785,200

(22) PCT Filed: Apr. 18, 2013

(86) PCT No.: PCT/JP2013/061486
§ 371 (c)(1),
(2) Date: Oct. 16, 2015

(87) PCT Pub. No.: WO2014/170985
PCT Pub. Date: Oct. 23, 2014

(65) Prior Publication Data
US 2016/0069803 A1   Mar. 10, 2016

(51) Int. Cl.
*G01N 21/59* (2006.01)
*G01N 33/49* (2006.01)
(Continued)

(52) U.S. Cl.
CPC ............ *G01N 21/59* (2013.01); *G01N 21/532* (2013.01); *G01N 21/85* (2013.01); *G01N 33/49* (2013.01); *G01N 33/4915* (2013.01)

(58) Field of Classification Search
CPC  G01N 21/05; G01N 33/4915; G01N 21/0303; G01N 2021/0346; G01N 21/03; G01N 21/59;G01N 21/031; G01N 21/8507; B01L 2300/0877; G01J 3/42; G01J 3/0291
(Continued)

(56) References Cited

U.S. PATENT DOCUMENTS 5,351,686 A * 10/1994 Steuer ................ A61B 5/14535
                                                              600/310
6,144,444 A * 11/2000 Haworth ............ A61B 5/14535
                                                              356/39
(Continued)

FOREIGN PATENT DOCUMENTS

JP    H03220444 A     9/1991
JP    H08313429 A     11/1996
(Continued)

OTHER PUBLICATIONS

AIPN Machine translation of Claims and Description of Japanese Document No. JP H09257705 to Suzuki (Oct. 1997).*
http://www.thefreedictionary.com/resin.*

*Primary Examiner* — Tarifur Chowdhury
*Assistant Examiner* — Mohamed K Amara
(74) *Attorney, Agent, or Firm* — Robert P. Michal, Esq.; Carter, DeLuca, Farrell & Schmidt, LLP

(57) ABSTRACT

A fluid concentration measuring device measures the concentration of a fluid flowing through a duct having a light-transmissive, deformable duct wall. The device includes a light source; a light receiving element which receives the light, which passed through the wall of the duct and the fluid inside the duct, and outputs a signal indicating the intensity of the light; light path distance setting means and fluid concentration output means which obtains a plurality of relational expressions, which indicate the relation between the light intensity and the fluid concentration when the light from the light supply part is received by the light receiving (Continued)

part over each of the light path distances, and obtains the fluid concentration from the light intensity at the light receiving part based on the relational expressions for the plurality of light path distances and outputs the fluid concentration.

10 Claims, 12 Drawing Sheets

(51) Int. Cl.
*G01N 21/53* (2006.01)
*G01N 21/85* (2006.01)

(58) Field of Classification Search
USPC ......... 356/440, 246, 436, 244, 432, 435, 73;
356/409; 250/576, 343, 339.12, 373;
435/288.7, 287.1, 288.4, 288.1, 288.3;
422/82.05, 82.09, 547
See application file for complete search history.

(56) References Cited

U.S. PATENT DOCUMENTS

| | | | |
|---|---|---|---|
| 2010/0110416 A1* | 5/2010 | Barrett | A61B 5/14535 356/40 |
| 2015/0238672 A1* | 8/2015 | Barrett | A61M 1/3621 356/40 |

FOREIGN PATENT DOCUMENTS

| | | |
|---|---|---|
| JP | H09257705 A | 10/1997 |
| JP | H10325797 A | 12/1998 |
| JP | 2003065952 A | 3/2003 |
| JP | 2005221298 A | 8/2005 |
| JP | 2006234549 A | 9/2006 |
| JP | 2007113979 A | 5/2007 |

* cited by examiner

FLUID CONCENTRATION MEASURING DEVICE

CROSS-REFERENCE TO RELATED APPLICATIONS

This application is a national phase entry under 35 U.S.C. 371 of PCT International Application PCT/JP2013/061486 filed Apr. 18, 2013, the entire disclosure of which is incorporated herein by reference.

TECHNICAL FIELD

The present invention relates to a device which measures the concentration of a fluid flowing through a light-transmissive, deformable duct based on the Beer-Lambert law.

BACKGROUND ART

Examples of conventionally known fluid concentration measuring devices include one described in Document 1. The measuring method and the measuring device described in Patent Literature 1 are employed for measuring the concentration of a treatment liquid as a fluid for washing treatment of semiconductor wafers. A plurality of measuring bodies are provided at intermediate positions of a treatment liquid supply pipe; light-transmissive portions having different light path lengths of light passing through the treatment liquid are provided inside the respective measuring bodies; light from a light source is supplied to one of the light-transmissive portions which has a light path length according to the properties of the treatment liquid; the light having passed through the treatment liquid at that light-transmissive portion is received by a light detector and the intensity of the light is measured; and the concentration of the treatment liquid is obtained from the light intensity based on the Beer-Lambert law.

PRIOR ART DOCUMENT

Patent Related Document

Document 1: Japanese Patent Application Laid-Open No. 10-325797

SUMMARY OF INVENTION

Technical Problem

In the conventional fluid concentration measuring device described above, since the exact light path length in each light-transmissive portion is known, the concentration of a fluid can be obtained easily by using a calculation formula for which the light path length is preset. On the other hand, it is contemplated that being able to measure the concentration of a fluid, such as blood or a chemical, flowing through a light-transmissive, deformable duct, e.g., a resin tube, would be greatly helpful in the medical field etc.

To apply the above conventional device to the concentration measurement of a fluid, such as blood or a chemical, flowing through a light-transmissive duct, such as a resin tube or a glass tube, it is necessary to pass light through a light path which extends across the light-transmissive duct. However, the inner diameter of the duct and the wall thickness of the duct constituting the light path length are both difficult to measure, and especially in the case of a resin tube having a deformable duct, the inner diameter may vary due to deformation. Thus, it is extremely difficult, and has been hitherto virtually impossible, to measure the concentration of blood, a chemical, etc. in such cases.

In this connection, the present inventors have previously proposed a fluid concentration measuring device which eliminates the influence of the inner diameter and the wall thickness of a duct from calculation based on the Beer-Lambert law by passing light from the same light source across a light-transmissive duct at a plurality of positions and obtaining the light intensity at each position (International Application No. PCT/JP2013/54664). However, in this measuring device, for the purpose of calculation, the light path inside the duct wall is set to be perpendicular to the duct wall at each light receiving part, while the actual light path extends obliquely across the duct wall, and moreover, the inclination angle of the light path varies at different refractive indexes. Thus, this device was found to have room for improvement to achieve higher calculation precision.

Solution to Problem

From this viewpoint, the present invention advantageously solves the problem with the conventional fluid concentration measuring device by fixedly disposing a light receiving part on the opposite side in a diametrical direction of a duct relative to a light supply part and maintaining the light path at a right angle to the longitudinal direction of the duct. According to the present invention, there is provided a fluid concentration measuring device which measures the concentration of a fluid flowing through a duct having a light-transmissive, deformable duct wall, the device including:

a light source which supplies light into the duct from a light supply part on the surface of the duct;

a light receiving element which receives the light, which has been supplied and passed through the wall of the duct and the fluid inside the duct, at a light receiving part located on the opposite side in the diametrical direction of the duct relative to the light supply part, and outputs a signal indicating the intensity of the light;

light path distance setting means which sets a plurality of light path distances between the light supply part and the light receiving part; and fluid concentration output means which, from the light intensity at the light receiving part located at each of the plurality of light path distances, obtains a plurality of relational expressions, which indicate the relation between the light intensity and the fluid concentration when the light from the light supply part is received by the light receiving part over each of the light path distances, based on the Beer-Lambert law, and obtains the fluid concentration from the light intensity at the light receiving part based on the relational expressions for the plurality of light path distances and outputs the fluid concentration.

Effects of Invention

In such a fluid concentration measuring device of the present invention, which measures the concentration of a fluid flowing through a duct having a light-transmissive, deformable duct wall, such as a resin tube, the light source supplies light into the duct from the light supply part on the surface of the duct; the light receiving element receives the light, which has been supplied and passed through the wall of the duct and the fluid inside the duct perpendicularly to the longitudinal direction of the duct, at the light receiving part located on the opposite side in the diametrical direction of the duct relative to the light supply part, and outputs a signal indicating the intensity of the light; the light path distance setting means sets a plurality of light path distances between the light supply part and the light receiving part; and, from the light intensity at the light receiving part located at each of the plurality of light path distances, the fluid concentration output means obtains a plurality of relational expressions, which indicate the relation between the light intensity and the fluid concentration when the light from the light supply part is received by the light receiving part over each of the light path distances, based on the Beer-Lambert law, and obtains the fluid concentration from the light intensity at the light receiving part based on the relational expressions for the plurality of light path distances and outputs the fluid concentration.

Thus, according to the fluid concentration measuring device of the present invention, since no light which has passed through a light path extending obliquely across the longitudinal direction of the duct is measured, it is possible to measure the concentration of a fluid, such as blood or a chemical, flowing through a duct having a light-transmissive, deformable duct wall, such as a resin tube, with high precision.

In the fluid concentration measuring device of the present invention, the light path distance setting means may have a plurality of pairs of light supply part and light receiving part having different intervals therebetween, and may change the light path distance by selectively using the pairs of light supply part and light receiving part. Thus, a plurality of light path distances can be set without changing the light path distance, so that the measuring time can be reduced.

In the fluid concentration measuring device of the present invention, the light path distance setting means may change the light path distance between the light supply part and the light receiving part by varying the interval between the light supply part and the light receiving part. Thus, it is possible to readily respond to changes in fluid concentration since the light path distance can be set arbitrarily, as well as to eliminate measurement errors due to differences among light sources or light receiving elements since a single light source and a single light receiving element are used.

In the fluid concentration measuring device of the present invention, the light path distance setting means may have a plurality of pairs of light supply part and light receiving part having different intervals therebetween, and one of the pairs of light supply part and light receiving part may be adapted so that the light path distance between the light supply part and the light receiving part of the one of the pairs is changed by varying the interval between the light supply part and the light receiving part. Thus, it is possible to readily respond to changes in fluid concentration since the light path distance can be set arbitrarily by using the pair of which the light path distance is to be changed. Once the relational expressions become known, the pair of a fixed light path distance can be used, so that the measurement time can be reduced and continuous, substantially real-time measurement can be performed.

In the fluid concentration measuring device of the present invention, the fluid concentration output means may use a table, which is obtained and stored in advance and shows the relation between the light intensity and the fluid concentration at the light receiving part located at each of the plurality of light path distances, to obtain the fluid concentration from the light intensity at the light receiving part and output the fluid concentration. The use of such a table makes it possible to quickly and easily obtain the fluid concentration from the light intensity at the light receiving part and output the fluid concentration.

EMBODIMENTS OF INVENTION

Figure 1:
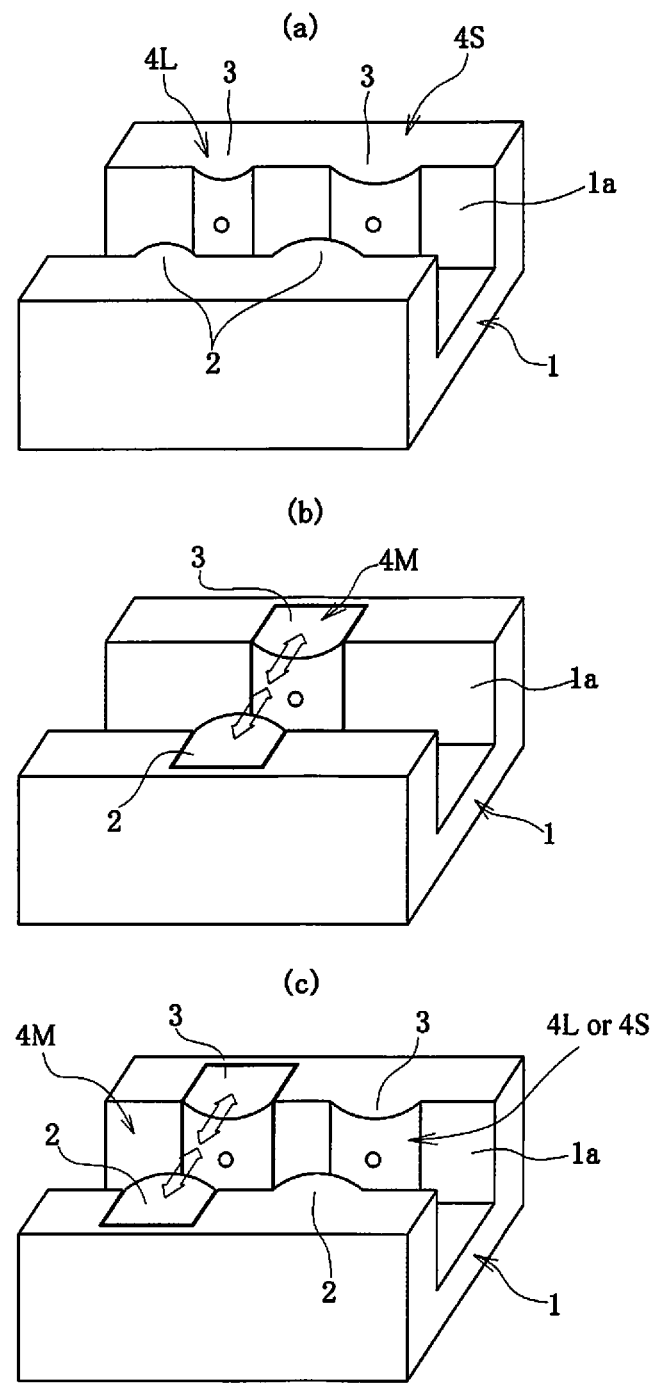
FIGS. 1(a) to 1(c) are schematic views respectively illustrating the external appearance of fluid concentration measuring devices of three types of embodiments of the present invention.

In the following, embodiments of the present invention will be described in detail by way of example based on the drawings. FIG. 1 to FIG. 5 are views illustrating the measurement principle and calculation method of fluid concentration in three types of embodiments of a fluid concentration measuring device of the present invention.

Specifically, FIGS. 1(a) to 1(c) are schematic views respectively illustrating the external appearance of the fluid concentration measuring devices of the three types of embodiments of the present invention. Each of the devices of the three types of embodiments shown in FIGS. 1(a) to 1(c) measures the concentration of blood as a fluid which flows through a substantially transparent resin tube as a duct having a light-transmissive, deformable duct wall. Here, the fluid concentration measuring device shown in FIG. 1(a) has two pairs of light emitting/receiving units 4 each of which is a pair of light emitting unit 2 and light receiving unit 3 which are fixed face-to-face on side walls of a groove 1a of a case 1 so as to hold a resin tube (not shown), which is passed through the groove 1a extending in the left-right direction in FIG. 1(a) in a central part of the case 1, therebetween and compressively deform the resin tube in the diametrical direction. These pairs of light emitting/receiving units 4 are of two different types: one is a short-distanced pair of units 4S, shown on the right side in FIG. 1(a), of which the light path distance between the light emitting unit 2 and the light receiving unit 3 is a predetermined short distance S; and the other is a long-distanced pair of units 4L, shown on the left side in FIG. 1(a), of which the light path distance between the light emitting unit 2 and the light receiving unit 3 is a predetermined long distance L. Accordingly, these two pairs of light emitting/receiving units 4 function as light path distance setting means. The two pairs of light emitting/receiving units 4 do not have to be adjacent to each other, and are preferably separated from each other to such an extent that the measurement is almost unaffected. In the case where the two pairs of light emitting/receiving units 4 are adjacent to each other, measurement by one pair of light emitting/receiving units 4 may be suspended while the other pair of light emitting/receiving units 4 is performing measurement.

The fluid concentration measuring device shown in FIG. 1(b) has one pair of light emitting/receiving units 4M which is a pair of light emitting unit 2 and light receiving unit 3 which are disposed face-to-face on both side walls of the groove 1a of the case 1 so as to hold a resin tube (not shown), which is passed through the groove 1a extending in the left-right direction in FIG. 1(b) in a central part of the case 1, therebetween and compressively deform the resin tube in the diametrical direction, and are supported on the case 1 so as to be movable in the directions toward/away from each other as indicated by the arrows in FIG. 1(b). This fluid concentration measuring device further has a light path distance change mechanism (not shown) which changes the light path distance between the light emitting unit 2 and the light receiving unit 3 of the pair of light emitting/receiving units 4M by relatively moving the light emitting unit 2 and the light receiving unit 3 in the directions toward/away from each other, i.e., in the diametrical direction of the resin tube. Accordingly, this light path distance change mechanism functions as the light path distance setting means.

The fluid concentration measuring device shown in FIG. 1(c) is a combination of a half of the device shown in FIG. 1(a) and the device shown in FIG. 1(b). That is, this fluid concentration measuring device has: one short-distanced pair of units 4S or one long-distanced pair of units 4L as the pair of light emitting/receiving units 4 which is a pair of light emitting unit 2 and light receiving unit 3 fixed face-to-face on the side walls of the groove 1a of the case 1 so as to hold a resin tube (not shown), which is passed through the groove 1a extending in the left-right direction in FIG. 1(c) in a central part of the case 1, therebetween and compressively deform the resin tube in the diametrical direction; and one pair of light emitting/receiving units 4M which is a pair of light emitting unit 2 and light receiving unit 3 which are disposed face-to-face on the side walls of the groove 1a of the case 1 so as to hold the resin tube therebetween and compressively deform the resin tube in the diametrical direction, and are supported on the case 1 so as to be movable in the directions toward/away from each other as indicated by the arrows in FIG. 1(c). This fluid concentration measuring device further has a light path distance change mechanism (not shown) which changes the light path distance between the light emitting unit 2 and the light receiving unit 3 of the pair of light emitting/receiving units 4M by relatively moving the light emitting unit 2 and the light receiving unit 3 in the directions toward/away from each other, i.e., in the diametrical direction of the resin tube. Accordingly, this light path distance change mechanism and the pair of light emitting/receiving units 4 with a fixed distance function as the light path distance setting means.

Here, the light emitting unit 2 has a built-in light emitting element, such as a light-emitting diode (LED) or a laser diode, as a light source which is supplied with electricity and emits light, and the light emitting unit 2 supplies the light from this light emitting element into the resin tube from a light supply part located on the surface of the resin tube. The light receiving unit 3 has a built-in light receiving element, such as a photodiode or a phototransistor, which receives light and generates electricity, and the light receiving unit 3 receives light which has been supplied from the light emitting unit 2 and passed through the interior of the resin tube, and outputs an electrical signal according to the intensity of the light. These light emitting unit 2 and light receiving unit 3 emit and receive light of a wavelength near 590 nm, as light for which oxygenated hemoglobin in arterial blood and deoxygenated hemoglobin in venous blood have roughly equal absorptive power.

Figure 2:
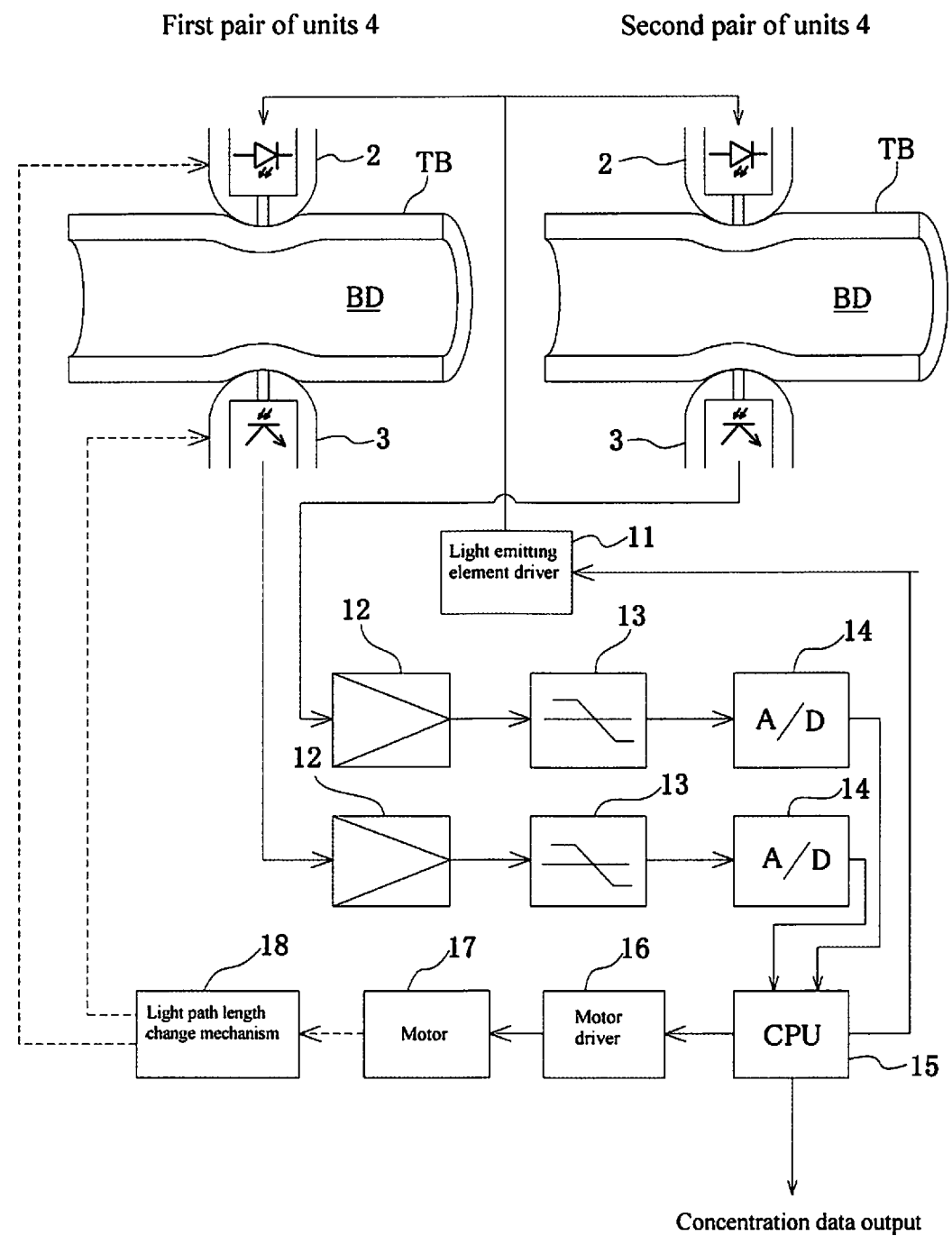
FIG. 2 is a block diagram collectively showing the electrical configuration of the fluid concentration measuring devices of the three types of embodiments.

FIG. 2 is a block diagram collectively showing the electrical configuration of the fluid concentration measuring devices of the three types of embodiments described above. In the case of the device shown in FIG. 1(a), one of the first pair of units 4 and the second pair of units 4 shown in FIG. 2 is the short-distanced pair of units 4S, and the other is the long-distanced pair of units 4L. Since the light path distances of these pairs of units 4 are fixed, this fluid concentration measuring device does not include a motor driver 16, a motor 17, and a light path distance change mechanism 18 to be described later.

In the device shown in FIG. 1(a), the light emitted from the light emitting elements inside the two light emitting units 2, which are each driven by a light emitting element driver 11, passes through the tube wall of a resin tube TB, which is held between the light emitting units 2 and the light receiving units 3 of the two pairs of units 4 and compressively deformed in the diametrical direction, on the side closer to the light emitting unit 2, blood BD flowing through the resin tube TB, and the tube wall on the side farther away from the light emitting unit 2 (on the opposite side), i.e., on the side closer to the light receiving unit 3. Then, the light passes through the light paths having different fixed distances, and is received by each of the light receiving elements inside the two light receiving units 3, and the light receiving elements inside the two light receiving units 3 each output an electrical signal of a level according to the intensity of the light received.

The output signals of the light receiving elements inside the two light receiving units 3 are each amplified by an amplifier 12, have high-frequency noise components removed by a low-pass filter 13, are converted by an analog-digital converter (A/D) 14 from an analog signal into a digital signal, and are input into a central processing unit (CPU) 15. The CPU 15 controls the operation of the light emitting element driver 11, and preferably selectively makes the light emitting units 2 of the two pairs of units 4 emit light so as to avoid interference between these light emitting units 2. In addition, the CPU 15 obtains the concentration of the blood BD inside the resin tube TB, as will be described later, from the output signals of the light receiving elements at the respective light path distances, and outputs a signal indicating data on the concentration. Accordingly, the CPU 15 functions as fluid concentration output means.

In the case of the device shown in FIG. 1(b), the first pair of units 4 shown in FIG. 2 is the pair of light emitting/receiving units 4M which is the pair of light emitting unit 2 and light receiving unit 3 disposed face-to-face on the side walls of the groove 1a of the case 1 and supported on the case 1 so as to be movable in the directions toward/away from each other. Having no second pair of units 4, this fluid concentration measuring device does not include the amplifier 12, the low-pass filter 13, and the A/D 14 which process the output signal from the light receiving element of the light receiving unit 3 of the second pair of units 4, but instead includes the motor driver 16, the motor 17, and the light path distance change mechanism 18 shown in FIG. 2 for the first pair of units 4.

The CPU 15, which functions as the fluid concentration output means, sends a control signal to the motor driver 16, and the motor driver 16 sends a driving current to the motor 17 according to this control signal. The motor 17 activates the light path distance change mechanism 18 according to the driving current, and the light path distance change mechanism 18 moves the light emitting unit 2 and the light receiving unit 3 of the first pair of units 4 in the directions toward/away from each other so as to vary the light path distance between the light emitting unit 2 and the light receiving unit 3, between the predetermined long distance L and the predetermined short distance S. One example of such a light path distance change mechanism 18 is a cam mechanism, to be described later, which moves at least one of the light emitting unit 2 and the light receiving unit 3, and moves preferably both units at the same time, in the directions toward/away from each other using a cam. Other than the cam mechanism, any mechanism, such as a screw mechanism may be used which rotates a drive shaft, having a right-hand male thread and a left-hand male thread at both ends, to thereby move the light emitting unit 2 and the light receiving unit 3, each having a female thread to screw-engage with each of the male threads, both at the same time in the directions toward/away from each other.

In the case of the device shown in FIG. 1(c), the first pair of units 4 shown in FIG. 2 is the pair of light emitting/receiving units 4M which is the pair of light emitting unit 2 and light receiving unit 3 disposed face-to-face on the side walls of the groove 1a of the case 1 and supported on the case 1 so as to be movable in the directions toward/away from each other, and the second pair of units 4 shown in FIG. 2 is the short-distanced pair of units 4S or the long-distanced pair of units 4L both having a fixed light path distance.

Figure 3:
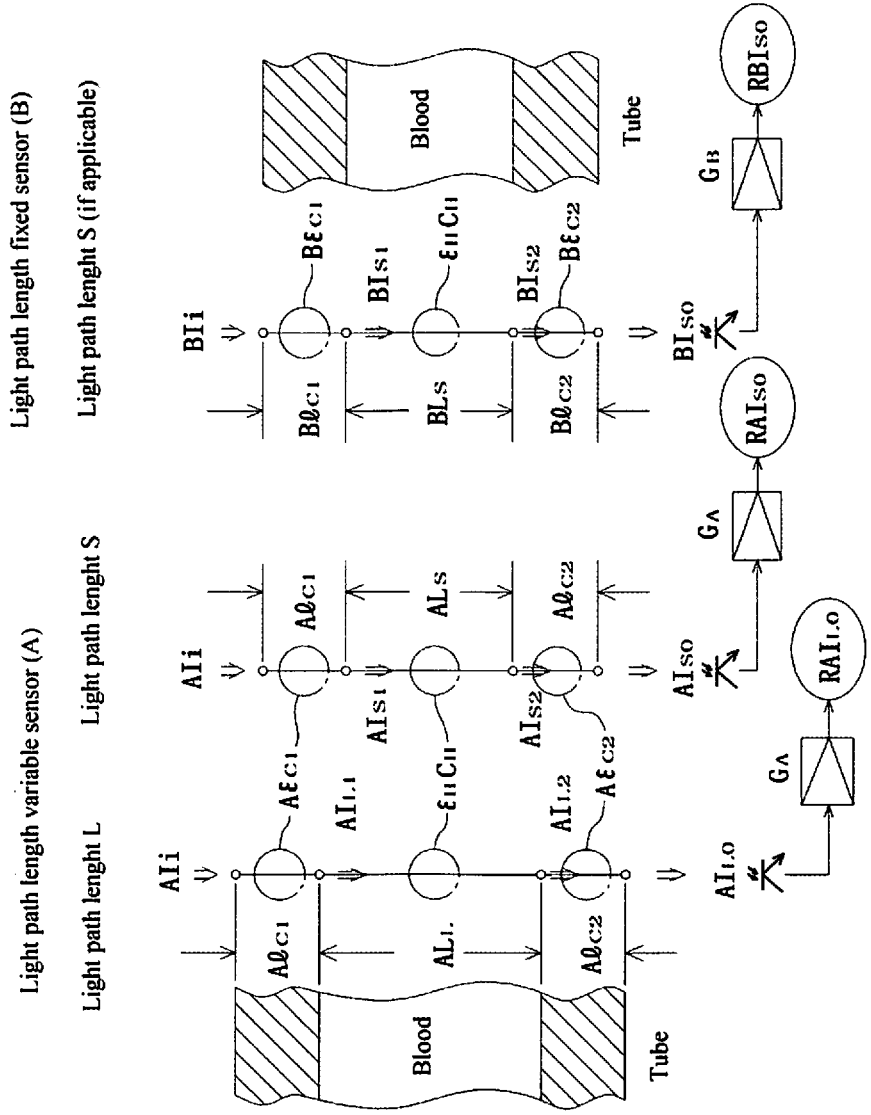
FIG. 3 is a view illustrating the symbols used in the embodiments along with the principle of the fluid concentration measuring device of the embodiment of FIG. 1(c).

FIG. 3 is a view illustrating the symbols used in the embodiments along with the principle of the fluid concentration measuring device of the embodiment of FIG. 1(c). For the movable pair of light emitting/receiving units (also referred to as a light path length variable sensor) 4M, in the case where the light path distance (light path length) is the long distance L, the thickness of the tube wall of the resin tube on the side closer to the light emitting unit 2 is $Al_{C1}$ (hereinafter written as $Al_{C1}$); the thickness of the tube wall of the resin tube on the side closer to the light receiving unit 3 is $Al_{C2}$ (hereinafter written as $Al_{C2}$); and the distance between these tube walls (short diameter of the tube inner diameter) is $AL_L$. In the case where the light path distance is the short distance S, on the assumption that the thickness of the tube wall remains the same even when the resin tube is pressed to some extent, the thickness of the tube wall of the resin tube on the side closer to the light emitting unit 2 is $Al_{C1}$; the thickness of the tube wall of the resin tube on the side closer to the light receiving unit 3 is $Al_{C2}$; and the distance between these tube walls is $AL_S$.

The absorption coefficient of the tube wall of the resin tube on the side closer to the light emitting unit 2 is $A\epsilon_{C1}$; the absorption coefficient of the tube wall of the resin tube on the side closer to the light receiving unit 3 is $A\epsilon_{C2}$; the absorption coefficient of the blood inside the resin tube is $\epsilon_H$; and the concentration of the blood is $C_H$. In the case where the light path distance is the long distance L, the incoming light intensity of the light from the light emitting unit 2 into the tube wall of the resin tube on the side closer to the light emitting unit 2 is $Ali$; the outgoing light intensity of the light from that tube wall is $AI_{L1}$; the outgoing light intensity of the light from the blood is $AI_{L2}$; the outgoing light intensity of the light from the tube wall of the resin tube on the side closer to the light receiving unit 3 into the light receiving unit 3 is $AI_{LO}$; the gain of the amplifier A connected with the light receiving unit 3 is $G_A$; and the output of the amplifier A is $RAI_{LO}$. In the case where the light path distance is the short distance S, the incoming light intensity of the light from the light emitting unit 2 into the tube wall of the resin tube on the side closer to the light emitting unit 2 is $Ali$; the outgoing light intensity of the light from that tube wall is $AI_{S1}$; the outgoing light intensity of the light from the blood is $AI_{S2}$; the outgoing light intensity of the light from the tube wall of the resin tube on the side closer to the light receiving unit 3 into the light receiving unit 3 is $AI_{SO}$; the gain of the amplifier A connected with the light receiving unit 3 is $G_A$; and the output of the amplifier A is $RAI_{SO}$.

For the fixed pair of light emitting/receiving units having the light path distance (light path length) of the short distance S (also referred to as a light path length fixed sensor) 4S, the thickness of the tube wall of the resin tube on the side closer to the light emitting unit 2 is $Bl_{C1}$ (hereinafter written as $Bl_{C1}$); the thickness of the tube wall of the resin tube on the side closer to the light receiving unit 3 is $Bl_{C2}$ (hereinafter written as $Bl_{C2}$); and the distance between these tube walls is $BL_S$. The absorption coefficient of the tube wall of the resin tube on the side closer to the light emitting unit 2 is $B\epsilon_{C1}$; the absorption coefficient of the tube wall of the resin tube on the side closer to the light receiving unit 3 is $B\epsilon_{C2}$; the absorption coefficient of the blood inside the resin tube is $\epsilon_H$; the concentration of the blood is $C_H$; the incoming light intensity of the light from the light emitting unit 2 into the tube wall of the resin tube on the side closer to the light emitting unit 2 is $Bli$; the outgoing light intensity of the light from that tube wall is $BI_{S1}$; the outgoing light intensity of the light from the blood is $BI_{S2}$; the outgoing light intensity of the light from the tube wall of the resin tube on the side closer to the light receiving unit 3 into the light receiving unit 3 is $BI_{SO}$; the gain of the amplifier A connected with the light receiving unit 3 is $G_B$; and the output of the amplifier A is $RBI_{SO}$.

To specifically explain these symbols: for example, of the incoming light intensities Ali and Bli, the symbols A and B represent two different sensors (the two different light path length fixed sensors, or the different light path length variable sensor and the light path length fixed sensor), I represents a light intensity, and i represents an input. Of the outgoing light intensities $AI_{LO}$ and $BI_{SO}$, the symbols A and B represent two different sensors, I represents a light intensity, L represents a long distance, S represents a short distance, and O represents an output. Of the light intensities $AI_{L1}$ and $BI_{S2}$, the symbols A and B represent two different sensors, I represents a light intensity, L represents a long distance, S represents a short distance, and the numbers 1 and 2 represent positions at which the light intensities are obtained. Of the absorption coefficients of the tube wall $A\epsilon_{C1}$ and $B\epsilon_{C2}$, the symbols A and B represent two different sensors, $\epsilon$ represents an absorption coefficient, C1 represents the tube wall on the side closer to the light emitting unit 2, and C2 represents the tube wall on the side closer to the light receiving unit 3. Of the tube wall thicknesses $Al_{C1}$ and $Bl_{C2}$, the symbols A and B represent two different sensors, l represents a tube wall thickness, C1 represents the tube wall on the side closer to the light emitting unit 2, and C2 represents the tube wall on the side closer to the light receiving unit 3. Of the distances between tube walls $AL_L$ and $BL_S$, the symbols A and B represent two different sensors, the first L represents a distance between the tube walls, the last L represents a long distance, and S represents a short distance. Of the gains $G_A$ and $G_B$, the symbol G represents an amplifier amplification factor including the sensitivity of the light receiving element, and A and B represent two different sensors. Of the amplifier outputs $RAI_{SO}$ and $RBI_{SO}$, the symbol R represents a value actually measured.

Figure 4:
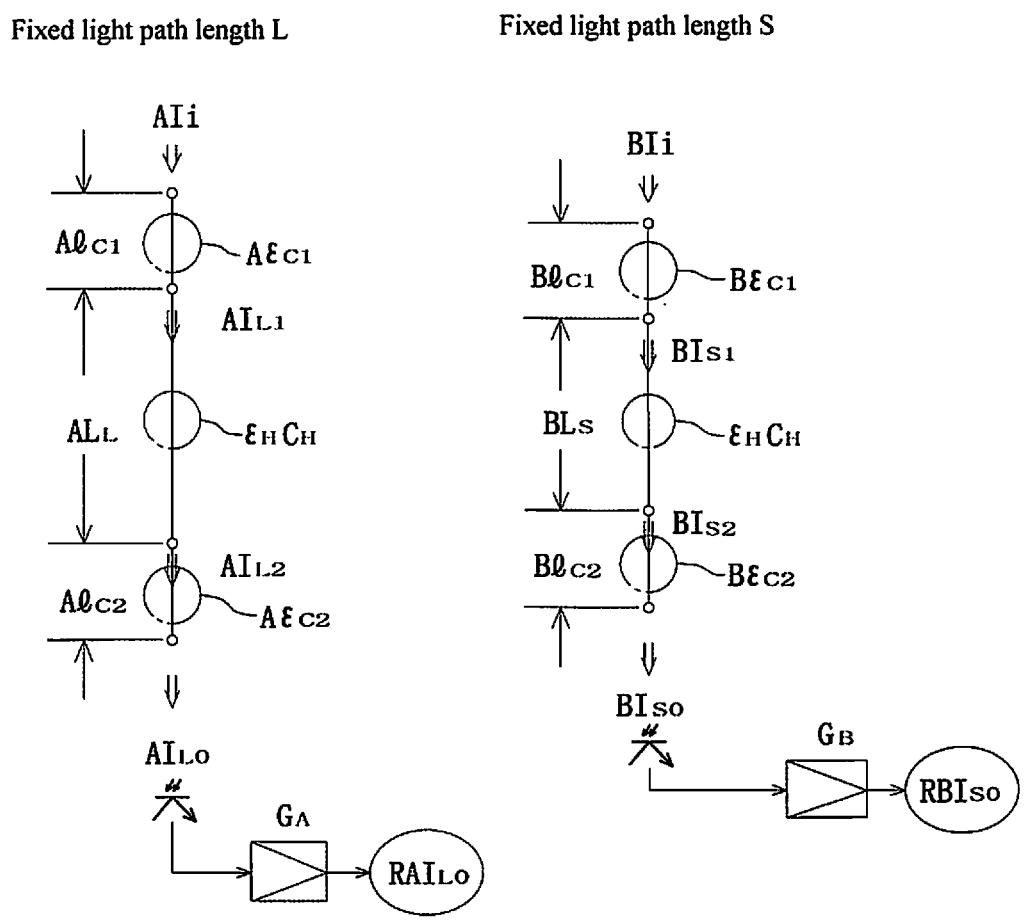
FIG. 4 is a view illustrating the principle of the fluid concentration measuring device of the embodiment of FIG. 1(a).

FIG. 4 shows the operation principle of the fluid concentration measuring device of the embodiment shown in FIG. 1(*a*). The device of this embodiment is provided with two types of light path, the light path of the fixed light path length L and the light path of the fixed light path length S, and here the possibility will be considered that the tube wall thickness, the tube wall composition, the incoming light intensity, and the amplifier amplification factor may be all different between these two types of light path.

First, let's look at the sensor A with the fixed light path length L. From the Beer-Lambert formula, the following formulae are derived:

[Formula 1]

$$AI_{L1} = Ali \times 10^{A\epsilon_{C1} \cdot Al_{C1}} \quad (1)$$

$$AI_{L2} = AI_{L1} \times 10^{\epsilon_H \cdot C_H \cdot AL_L} \quad (2)$$

$$AI_{LO} = AI_{L2} \times 10^{A\epsilon_{C2} \cdot Al_{C2}} \quad (3)$$

$$RAI_{LO} = AI_{LO} \times G_A \quad (4)$$

From the formulae (1) to (4), the following formula is obtained:

[Formula 2]

$$AI_{LO} = \frac{RAI_{LO}}{G_A} = Ali \times 10^{A\epsilon_{C1} \cdot Al_{C1}} \times 10^{\epsilon_H \cdot C_H \cdot AL_L} \times 10^{A\epsilon_{C2} \cdot Al_{C2}} \quad (5)$$

Similarly, for the sensor B with the fixed light path length S, the following formulae are derived:

[Formula 3]

$$BI_{S1} = Bli \times 10^{B\epsilon_{C1} \cdot Bl_{C1}} \quad (6)$$

$$BI_{S2} = BI_{S1} \times 10^{\epsilon_H \cdot C_H \cdot BL_S} \quad (7)$$

$$BI_{SO} = BI_{S2} \times 10^{B\epsilon_{C2} \cdot Bl_{C2}} \quad (8)$$

$$RBI_{SO} = BI_{SO} \times G_B \quad (9)$$

From the Formulae (6) to (9), the Following Formula is Obtained:

[Formula 4]

$$BI_{SO} = \frac{RBI_{SO}}{G_B} = Bli \times 10^{B\epsilon_{C1} \cdot Bl_{C1}} \times 10^{\epsilon_H \cdot C_H \cdot BL_S} \times 10^{B\epsilon_{C2} \cdot Bl_{C2}} \quad (10)$$

Dividing the formula (5) by the formula (10) gives the following formula:

[Formula 5]

$$\frac{AI_{LO}}{BI_{SO}} = \frac{\frac{RAI_{LO}}{G_A}}{\frac{RBI_{SO}}{G_B}} = \frac{Ali \times 10^{A\epsilon_{C1} \cdot Al_{C1}} \times 10^{\epsilon_H \cdot C_H \cdot AL_L} \times 10^{A\epsilon_{C2} \cdot Al_{C2}}}{Bli \times 10^{B\epsilon_{C1} \cdot Bl_{C1}} \times 10^{\epsilon_H \cdot C_H \cdot BL_S} \times 10^{B\epsilon_{C2} \cdot Bl_{C2}}}$$

Hence, $$\frac{RAI_{LO}}{RBI_{SO}} = \frac{G_A}{G_B} \times \frac{Ali}{Bli} \times \frac{Ali \times 10^{A\epsilon_{C1} \cdot Al_{C1}} \times 10^{\epsilon_H \cdot C_H \cdot AL_L} \times 10^{A\epsilon_{C2} \cdot Al_{C2}}}{Bli \times 10^{B\epsilon_{C1} \cdot Bl_{C1}} \times 10^{\epsilon_H \cdot C_H \cdot BL_S} \times 10^{B\epsilon_{C2} \cdot Bl_{C2}}}$$

Taking the logarithm of both sides based on $AL_L - BL_S = DL$ gives the following formula:

[Formula 6]

$$\log\left(\frac{RAI_{LO}}{RBI_{SO}}\right) = \log\left(\frac{G_A}{G_B}\right) + \log\left(\frac{Ali}{Bli}\right) + \epsilon_H \cdot C_H \cdot DL +$$
$$A\epsilon_{C1} \cdot Al_{C1} + A\epsilon_{C2} \cdot Al_{C2} - B\epsilon_{C1} \cdot Bl_{C1} - B\epsilon_{C2} \cdot Bl_{C2}$$

Here, the terms on the right side of the above formula other than $\epsilon_H \cdot C_H \cdot DL$ of the third term are constant. With these constant terms substituted by K, this formula is expressed as follows:

[Formula 7]

$$\log\left(\frac{RAI_{LO}}{RBI_{SO}}\right) = \epsilon_H \cdot C_H \cdot DL + K$$

Thus, the blood concentration $C_H$ inside the resin tube is obtained by the following formula:

[Formula 8]

$$C_H = \frac{1}{\epsilon_H \cdot DL}\left(\log\frac{RAI_{LO}}{RBI_{SO}} - K\right) \quad (11)$$

where, $$K = \log\frac{G_A}{G_B} + \log\frac{Ali}{Bli} + A\epsilon_{C1} \cdot Al_{C1} +$$
$$A\epsilon_{C2} \cdot Al_{C2} - B\epsilon_{C1} \cdot Bl_{C1} - B\epsilon_{C2} \cdot Bl_{C2}$$

Since the distance between the sensors A and B in the device of this embodiment is about 1 cm, when the tube wall absorption coefficients $A\epsilon_{C1}$, $A\epsilon_{C2}$, $B\epsilon_{C1}$, and $B\epsilon_{C2}$ are regarded as equal, and the tube wall thicknesses $Al_{C1}$, $Al_{C2}$, $Bl_{C1}$, and $Bl_{C2}$ are also regarded as equal, this formula can be simplified as follows:

[Formula 9]
$$K = \log\frac{G_A}{G_B} + \log\frac{Ali}{Bli}$$

In the device of this embodiment, DL can be set to 0.5 mm, for example.

Since the symbol K in the formula (11) is a value including all the differences in incoming light intensity, amplification factor, tube wall thickness, and tube wall composition, this formula shows that the measurement output of the device can be corrected to a correct value if K is calculated by assigning an exact value of the blood concentration $C_H$ which is separately obtained outside the device.

Figure 5:
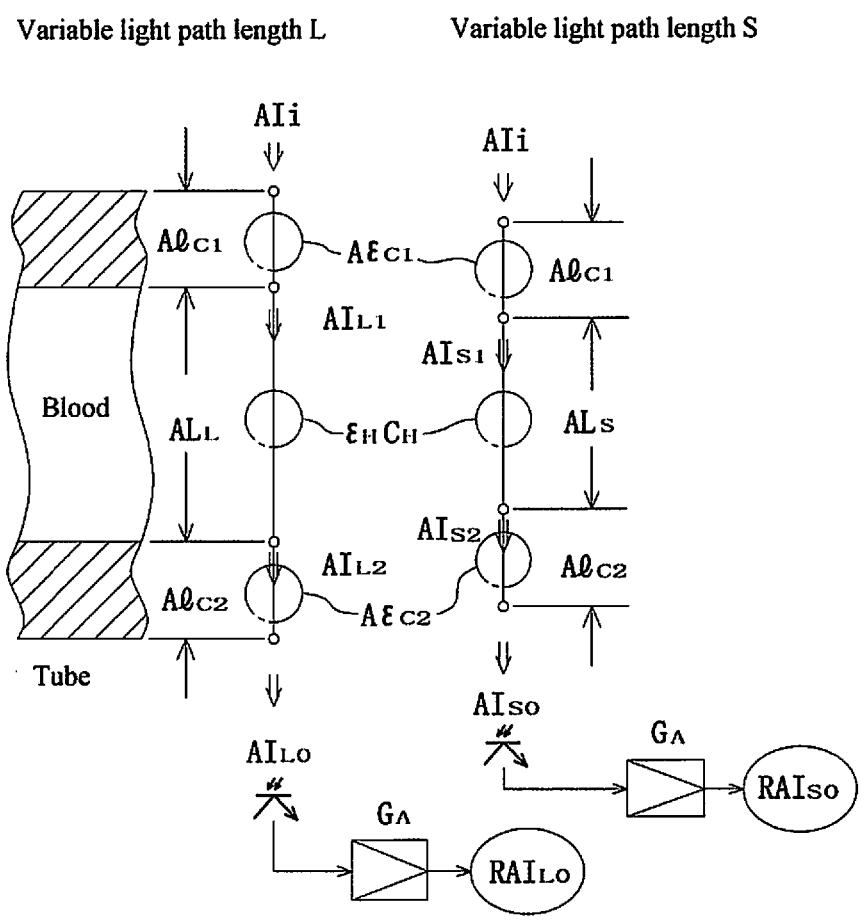
FIG. 5 is a view illustrating the principle of the fluid concentration measuring device of the embodiment of FIG. 1(b).

FIG. 5 shows the operation principle of the fluid concentration measuring device of the embodiment shown in FIG. 1(b). The device of this embodiment is provided with one light path of a variable light path length. Since the two types of light path length L, S are mechanically created on this one light path by the light path distance change mechanism 18, data can be measured under two types of conditions which are different from each other only in light path length, and exactly the same in tube wall thickness, tube wall composition, incoming light intensity, and amplifier amplification factor. Thus, concentration measurement values can be obtained with high precision without any maintenance performed between measurements.

First, let's look at the case where the light path length is L. From the Beer-Lambert formula, the following formulae are derived:

[Formula 10]

$$AI_{L1} = Ali \times 10^{A\varepsilon C1 \cdot AlC1} \quad (12)$$

$$AI_{L2} = AI_{L1} \times 10^{\varepsilon_H \cdot C_H \cdot AL_L} \quad (13)$$

$$AI_{LO} = AI_{L2} \times 10^{A\varepsilon C2 \cdot AlC2} \quad (14)$$

$$RAI_{LO} = AI_{LO} \times G_A \quad (15)$$

From the formulae (12) to (15), the following formula is obtained:

[Formula 11]

$$AI_{LO} = \frac{RAI_{LO}}{G_A} = Ali \times 10^{A\varepsilon C1 \cdot AlC1} \times 10^{\varepsilon_H \cdot C_H \cdot AL_L} \times 10^{A\varepsilon C2 \cdot AlC2} \quad (16)$$

Similarly, in the case where the light path length is S, the following formulae are derived:

[Formula 12]

$$AI_{S1} = Ali \times 10^{A\varepsilon C1 \cdot AlC1} \quad (17)$$

$$AI_{S2} = AI_{S1} \times 10^{\varepsilon_H \cdot C_H \cdot AL_S} \quad (18)$$

$$AI_{SO} = AI_{S2} \times 10^{A\varepsilon C2 \cdot AlC2} \quad (19)$$

$$RAI_{SO} = AI_{SO} \times G_A \quad (20)$$

From the formulae (17) to (20), the following formula is obtained:

[Formula 13]

$$AI_{SO} = \frac{RAI_{SO}}{G_A} = Ali \times 10^{A\varepsilon C1 \cdot AlC1} \times 10^{\varepsilon_H \cdot C_H \cdot AL_S} \times 10^{A\varepsilon C2 \cdot AlC2} \quad (21)$$

Dividing the formula (16) by the formula (21) gives the following formula:

[Formula 14]

$$\frac{AI_{LO}}{AI_{SO}} = \frac{\frac{RAI_{LO}}{G_A}}{\frac{RAI_{SO}}{G_A}} = \frac{Ali \times 10^{A\varepsilon C1 \cdot AlC1} \times 10^{\varepsilon_H \cdot C_H \cdot AL_L} \times 10^{A\varepsilon C2 \cdot AlC2}}{Ali \times 10^{B\varepsilon C1 \cdot BlC1} \times 10^{\varepsilon_H \cdot C_H \cdot BL_S} \times 10^{B\varepsilon C2 \cdot BlC2}}$$

Hence, $$\frac{RAI_{LO}}{RAI_{SO}} = 10^{\varepsilon_H \cdot C_H \cdot (AL_L - AL_S)}$$

Taking the logarithm of both sides based on $AL_L - AL_S = DL$ gives the following formula:

[Formula 15]

$$\log\left(\frac{RAI_{LO}}{RAI_{SO}}\right) = \varepsilon_H \cdot C_H \cdot DL$$

Thus, the blood concentration $C_H$ inside the resin tube is obtained by the following formula:

[Formula 16]

$$C_H = \frac{1}{\varepsilon_H \cdot DL}\left(\log\frac{RAI_{LO}}{RAI_{SO}}\right) \quad (22)$$

This formula (22) shows that the blood concentration $C_H$ can be obtained from the amplifier outputs $RAI_{LO}$, $RAI_{SO}$ which are obtained by measuring with the light path distance L and the light path distance S switched, and that the calculation is not affected by the difference in incoming light intensity or the difference in tube wall composition. However, it is necessary to switch between the light path lengths at each measurement.

As described above, FIG. 3 shows the operation principle of the fluid concentration measuring device of the embodiment shown in FIG. 1(c). The device of this embodiment has one first pair of units 4M with a variable light path length (light path length variable sensor (A)), shown on the left side in FIG. 2, which sets light paths of the light path distances L and S inside the resin tube, and one second pair of units 4L or 4S with a fixed light path length (light path length fixed sensor (B)), shown on the right side in FIG. 2, which sets a light path of the light path distance L or S inside the resin tube. This device further includes the motor driver 16, the motor 17, and the light path distance change mechanism 18, as with the device of the embodiment shown in FIG. 1(b), in order to set the light paths of the light path distances L and S by varying the distance between the light emitting unit 2 and the light receiving unit 3 of the first pair of units 4M.

First, in step S1, the fluid concentration measuring device of the embodiment shown in FIG. 1(c) sets the light paths of the light path distances L and S by the first pair of units 4M with a variable light path length, and obtains correction data by performing high-precision measurement under the same conditions except for the distance between the tube walls inside the resin tube. Then, in step S2, in the case where the second pair of units is the pair of units 4L of which the light path length is the long distance L, the fluid concentration measuring device fixes the light path length of the first pair of units 4M to the short distance S, and in the case where the second pair of units is the pair of units 4S of which the light path length is the short distance S, the device fixes the light path length of the first pair of units 4M to the long distance L, to have the same configuration as the device shown in FIG. 1(a), and performs the subsequent measurement using the correction data obtained previously. According to the device of the embodiment shown in FIG. 1(c), it is not necessary to switch between two types of light path length for each measurement and the correction data can be obtained within the device, so that high-precision measurement can be performed continuously.

Specifically, in the step S1, since the configuration is the same as that of the device of the embodiment shown in FIG. 1(b), the blood concentration $C_H$ can be obtained by the formula (22) from the values measured at the two types of light path length of the first pair of units 4M:

[Formula 17]
$$C_H = \frac{1}{\varepsilon_H \cdot DL}\left(\log\frac{RAI_{LO}}{RAI_{SO}}\right)$$

In the step S2, since the configuration is the same as that of the device of the embodiment shown in FIG. 1(a), the blood concentration $C_H$ can be obtained by the formula (11), for example, from the measurement value of the first pair of units 4M of the light path length L and the measurement value of the second pair of units 4S of the light path length S:

[Formula 18]
$$C_H = \frac{1}{\varepsilon_H \cdot DL}\left(\log\frac{RAI_{LO}}{RBI_{SO}} - K\right)$$

Combining these formulae gives the following formula:

[Formula 19]
$$\log\left(\frac{RAI_{LO}}{RAI_{SO}}\right) = \log\left(\frac{RAI_{LO}}{RBI_{SO}}\right) - K$$

Hence, $$K = \log\left(\frac{RAI_{LO}}{RBI_{SO}}\right) - \log\left(\frac{RAI_{LO}}{RAI_{SO}}\right)$$
$$= \log\left(\frac{\frac{RAI_{LO}}{RBI_{SO}}}{\frac{RAI_{LO}}{RAI_{SO}}}\right)$$
$$= \log\left(\frac{RAI_{SO}}{RBI_{SO}}\right)$$

Thus, the correction factor K can be obtained to be used for the measurement in the step S2.

Figure 6:
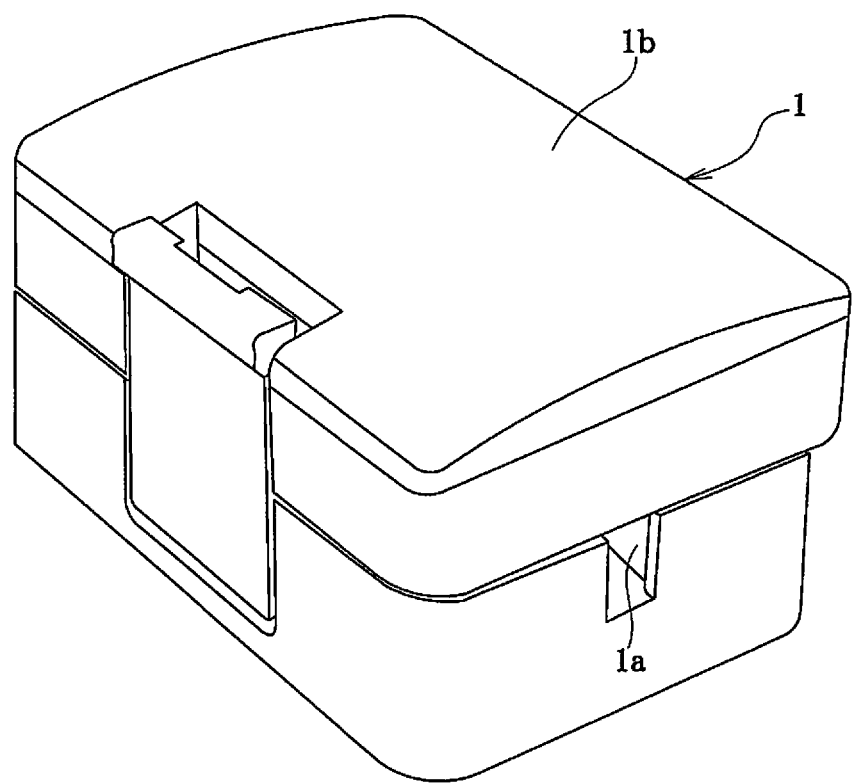
FIG. 6 is a view illustrating a configuration example of the fluid concentration measuring device of the embodiment of FIG. 1(b) with a lid closed.
Figure 7:
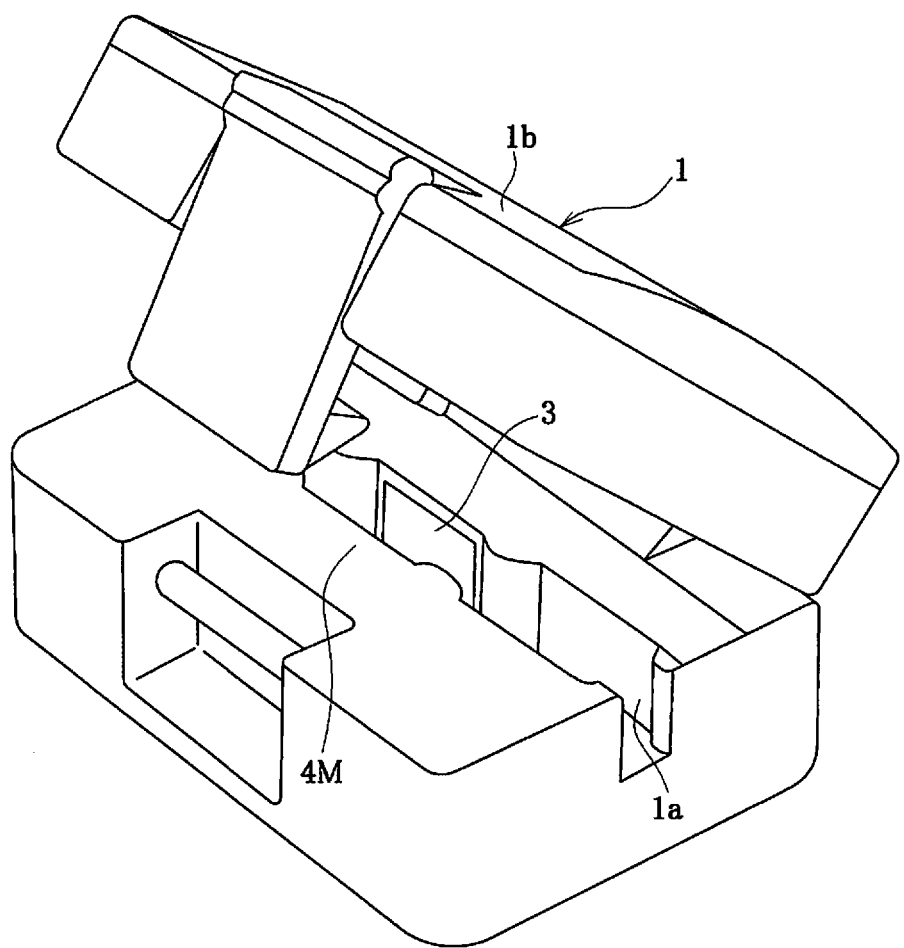
FIG. 7 is a view illustrating the configuration example of the fluid concentration measuring device of the embodiment of FIG. 1(b) with the lid open.

FIG. 6 is a view illustrating a more specific example of the configuration of the fluid concentration measuring device of the embodiment of FIG. 1(b) with a lid closed, and FIG. 7 is a view illustrating the fluid concentration measuring device of the configuration example with the lid open. The device of this configuration example includes the case 1 having a lid 1b which can be opened/closed through a hinge, and the groove 1a extending in the obliquely left-right direction in FIGS. 6 and 7 in a central part when the lid 1b is open. The device of this configuration example further includes one pair of light emitting/receiving units 4M (only the light receiving unit 3 is shown in FIGS. 6 and 7) which is a pair of light emitting unit 2 and light receiving unit 3 disposed face-to-face on both side walls of the groove 1a of the case 1 and supported on the case 1 so as to be movable in the directions toward/away from each other.

Figure 8:
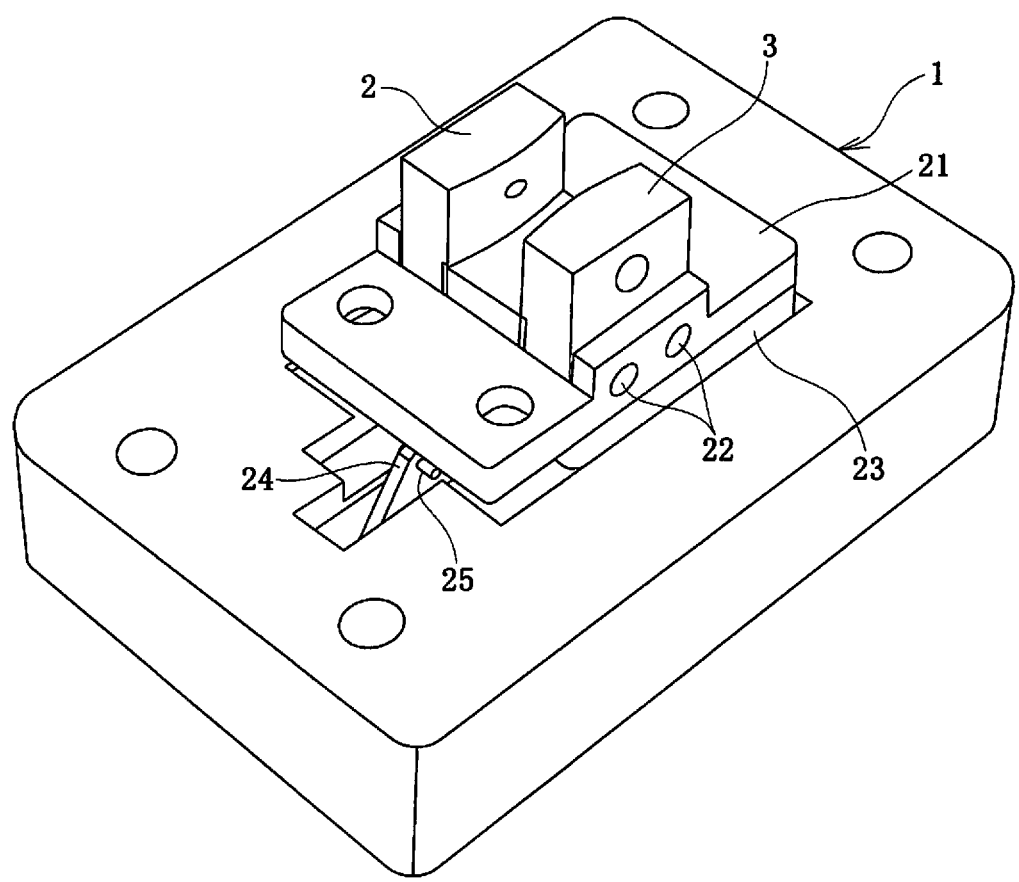
FIG. 8 is a view illustrating a pair of internal light emitting unit and light receiving unit in the configuration example of the fluid concentration measuring device of the embodiment of FIG. 1(b).
Figure 9:
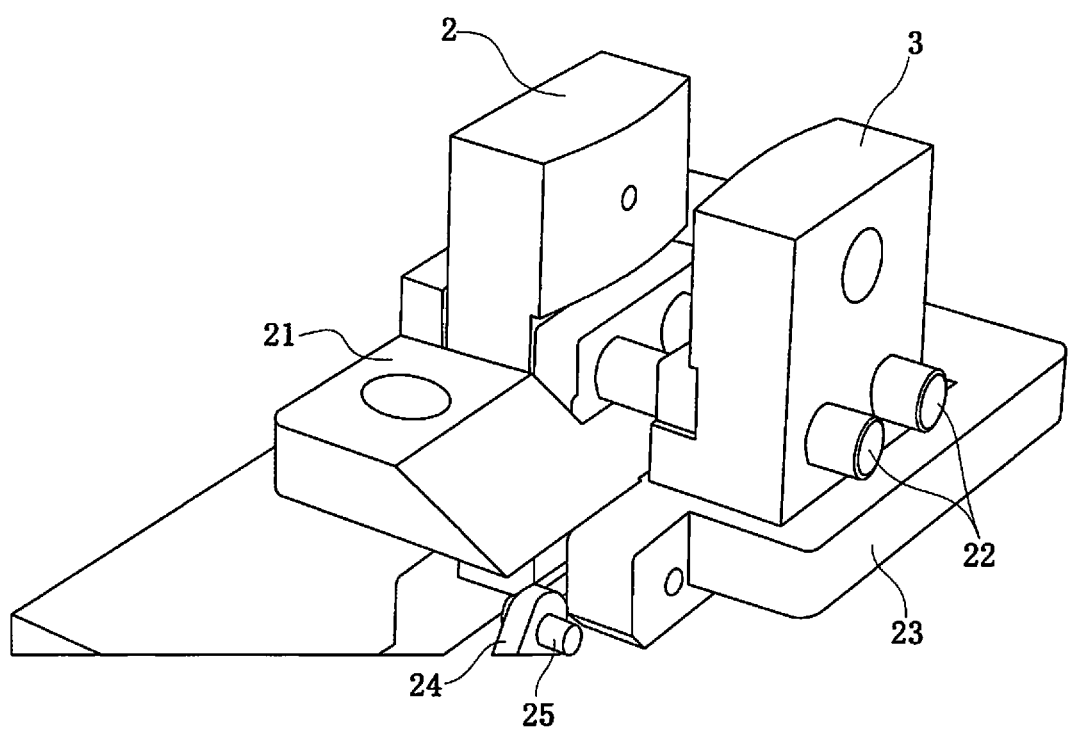
FIG. 9 is a view illustrating a guide mechanism, partially cut away, which guides relative movement of the internal light emitting unit and light receiving unit in the configuration example of the fluid concentration measuring device of the embodiment of FIG. 1(b).

FIG. 8 is a view showing the pair of light emitting unit 2 and light receiving unit 3 inside the fluid concentration measuring device of the configuration example, and FIG. 9 is a view showing a guide mechanism, partially cut away, which guides relative movement of the light emitting unit 2 and the light receiving unit 3 inside the fluid concentration measuring device of the configuration example. In FIGS. 8 and 9, a deck part of the case 1 which covers the pair of light emitting unit 2 and light receiving unit 3 and forms the groove 1a is not shown. As shown in FIG. 9, two guide rods 22 are fixed on a baseplate 21 fixed inside the case 1, and the light emitting unit 2 and the light receiving unit 3, while facing each other, slidably fit with these guide rods 22 and can relatively move in the directions toward/away from each other, i.e., in the diametrical direction of the resin tube. Under this baseplate 21, a cam plate 23 is disposed so as to be slidable in the longitudinal direction of the groove 1a, which is orthogonal to the longitudinal direction of the guide rods 22, along the lower surface of the baseplate 21.

Figure 10:
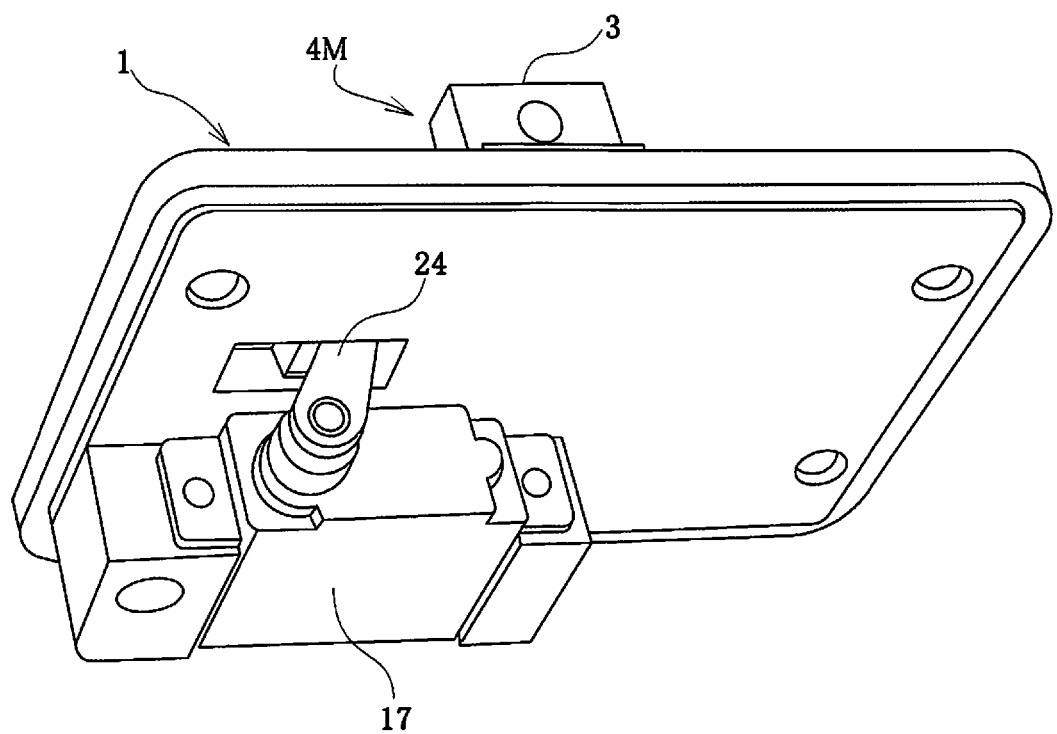
FIG. 10 is a view illustrating a motor-driven crank mechanism which changes the relative interval between the internal light emitting unit and light receiving unit in the configuration example of the fluid concentration measuring device of the embodiment of FIG. 1(b).
Figure 11:
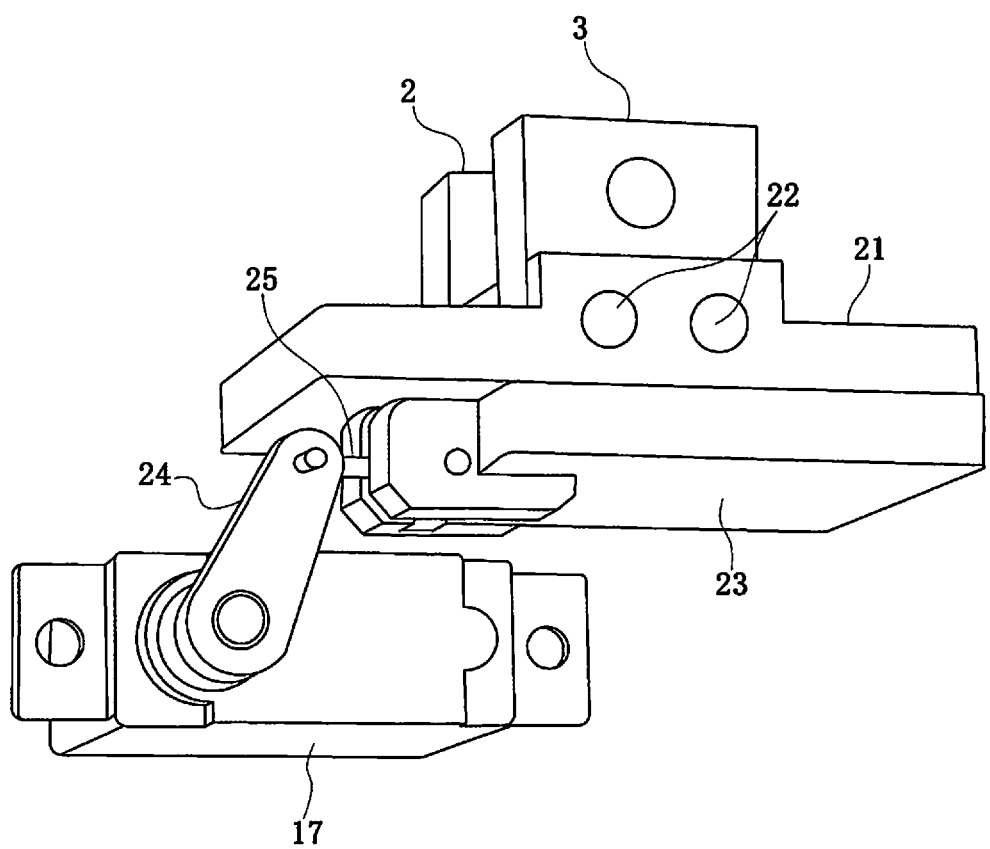
FIG. 11 is a view illustrating a state of connection between a cam plate and the crank mechanism which change the relative interval between the internal light emitting unit and light receiving unit in the configuration example of the fluid concentration measuring device of the embodiment of FIG. 1(b).
Figure 12:
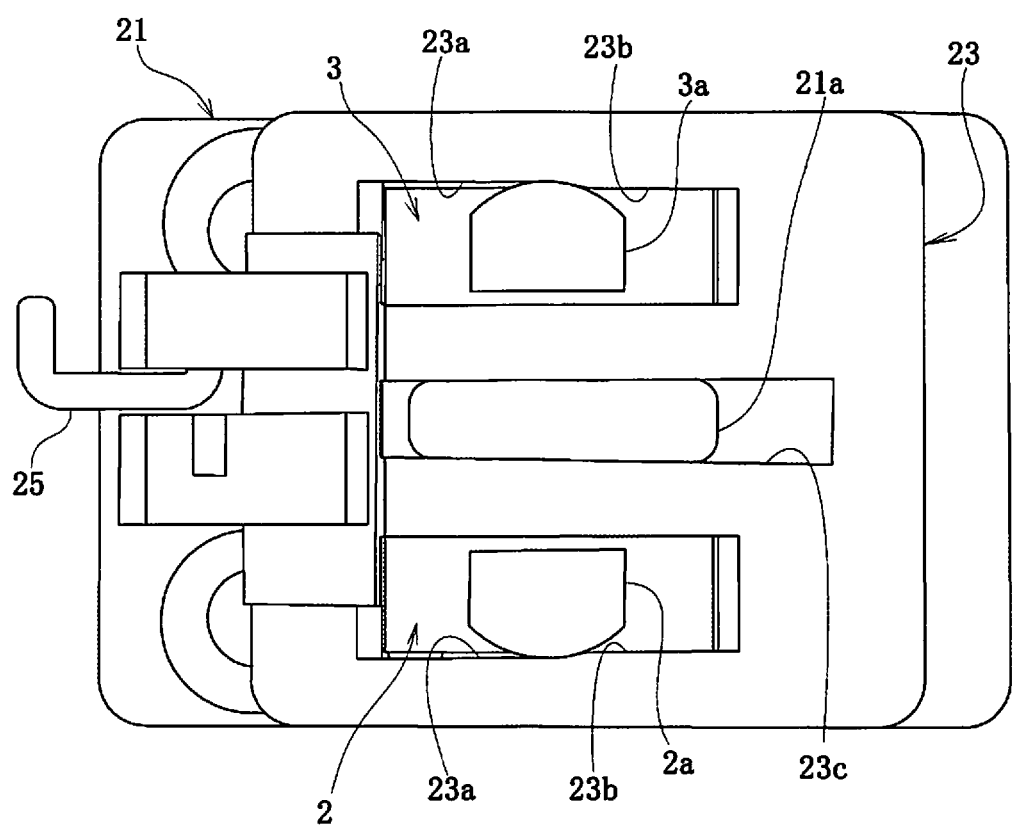
FIG. 12 is a view illustrating the configuration of the cam plate which changes the relative interval between the internal light emitting unit and light receiving unit in the configuration example of the fluid concentration measuring device of the embodiment of FIG. 1(b).

FIG. 10 is a view illustrating a motor-driven crank mechanism which changes the relative interval between the light emitting unit and the light receiving unit inside the fluid concentration measuring device of the configuration example. FIG. 11 is a view illustrating a state of connection between the cam plate and the crank mechanism inside the fluid concentration measuring device of the configuration example. FIG. 12 is a view illustrating the configuration of the cam plate of the fluid concentration measuring device of the configuration example. As shown in the back view of FIG. 10, a base portion of a crank arm 24 is fixed on the output shaft of the motor 17, which is constituted by a servomotor with a speed reducer and housed and fixed inside the case 1, and a leading end portion of this crank arm 24 is connected with one end of the cam plate 23 through a link member 25 as shown in FIG. 11. Thus, the crank mechanism is configured which advances/retracts the cam plate 23 in the longitudinal direction of the groove 1a of the case 1.

FIG. 12 is a view illustrating the configuration of the cam plate which changes the relative interval between the light emitting unit and the light receiving unit inside the fluid concentration measuring device of the configuration example. Here, the cam plate 23 has two pairs of cam surfaces 23a, 23b each making a pair in the direction in which the cam surfaces are facing each other, in the vicinity of both sides of the cam plate 23 which are located on the upper and lower sides in FIG. 12, and a guide hole 23c which extends in the left-right direction in FIG. 12 in a central part of the cam plate 23. The distance between the cam surfaces 23a, which make one of the pairs, is slightly larger than the distance between the cam surfaces 23b making the other pair, and the difference between these distances corresponds to the difference DL between the longer distance between the tube walls $AL_L$ and the shorter distance between the tube walls $AL_S$.

The cam surfaces 23a, 23b in the vicinity of each side of the cam plate 23 are connected smoothly with each other through a curved surface. Convexly curved surfaces of cam follower portions 2a, 3a, which are protruding from the lower end of the light emitting unit 2 and the light receiving unit 3, respectively, are in sliding contact with the two pairs of cam surfaces 23a, 23b, while facing these cam surfaces 23a, 23b. A compression spring (not shown) is inserted between the light emitting unit 2 and the light receiving unit 3. This compression spring is always urging the light emitting unit 2 and the light receiving unit 3 in the direction away from each other to maintain the sliding contact between the convexly curved surfaces of the cam follower portions 2a, 3a and the cam surfaces 23a, 23b, and the cam mechanism is configured by these members.

A ridge 21a projecting from the lower surface of the baseplate 21 is slidably fitted in the guide hole 23c in a central part of the cam plate 23, and thereby the guide mechanism is configured which guides movement of the cam plate 23 in the longitudinal direction of the groove 1a of the case 1. By these crank mechanism, cam mechanism, and guide mechanism, a light path distance change mechanism 26 is configured which changes the light path distance between the light emitting unit 2 and the light receiving unit 3, between the long distance and the short distance.

In the fluid concentration measuring device of such a configuration example, when the motor 17 turns the crank arm 24 to a predetermined position, the link member 25 advances/retracts the cam plate 23 in the longitudinal direction of the groove 1a of the case 1 to a position at which the convexly curved surfaces of the cam follower portions 2a, 3a protruding from the lower ends of the light emitting unit 2 and the light receiving unit 3, respectively, come into contact with the cam surface 23a or the cam surface 23b, and sets the light path distance between the light emitting unit 2 and the light receiving unit 3 to the predetermined long distance or the predetermined short distance. Thus, according to this configuration example, it is possible to configure the mechanical part of the fluid concentration measuring device of the embodiment shown in FIG. 1(b) and measure the blood concentration with high precision.

Though the embodiments have been described based on the examples shown in the drawings, the present invention is not limited to the embodiments described above, but can be appropriately modified within the scope of claims. For example, in the devices of the above embodiments, the CPU 15 obtains the blood concentration by performing the arithmetic process based on the light intensity at the light receiving unit 3 and outputs this blood concentration. Instead, the CPU 15 may use a table, which is obtained and stored in advance and shows the relation between the light intensity and the fluid concentration at the light receiving part located at each of the plurality of light path distances, to obtain the fluid concentration from the light intensity at the light receiving part and output the fluid concentration.

In the devices of the above embodiments, light of a wavelength near 590 nm is used as light for which oxygenated hemoglobin in arterial blood and deoxygenated hemoglobin in venous blood have roughly equal absorptive power. Instead, light of a wavelength near 520 nm, 550 nm, 570 nm, or 805 nm, for example, may be used.

In the devices of the above embodiments, the concentration of blood as a liquid is measured. Instead, the devices can also be used for measuring the concentration of other liquids, and in that case, it is preferable that light of a wavelength for which the liquid has high absorptive power is selected as the light to be supplied from the light source, as such light is more likely to exhibit a difference in intensity at the light receiving part according to the duct wall thickness etc.

In the devices of the above embodiments, light is supplied from the light supply part at the two types of light path distance, and the light is received and the intensity of the light is obtained by the light receiving part. Instead, three or more types of light path distance may be set and the light intensity at each light receiving part may be obtained. Thus, the measurement precision can be further enhanced, for example, by averaging the results obtained.

INDUSTRIAL APPLICABILITY

According to the fluid concentration measuring device of the present invention, since no light which has passed through a light path extending obliquely across the longitudinal direction of a duct is measured, it is possible to measure the concentration of a fluid, such as blood or a chemical, flowing through a duct having a light-transmissive, deformable duct wall, such as a resin tube, with high precision.

EXPLANATION OF REFERENCE NUMERALS

1 Case
1a Groove
1b Lid
2 Light emitting unit
2a, 3a Cam follower portion
3 Light receiving unit
4 Pair of light emitting/receiving units
4L Long-distanced pair of light emitting/receiving units
4M Pair of light emitting/receiving units with variable light path length
4S Short-distanced pair of light emitting/receiving units
11 Light emitting element driver
12 Amplifier
13 Low-pass filter
14 Analog-digital converter
15 CPU
16 Motor driver
17 Motor
18 Light path distance change mechanism
21 Baseplate
21a Ridge
22 Guide rod
23 Cam plate
23a, 23b Cam surface
23c Guide hole
24 Crank arm
25 Link member
26 Light path distance change mechanism
TB Resin tube
BD Blood

The invention claimed is:

1. A fluid concentration measuring device which measures concentration of a fluid flowing through a resin tube being light-transmissive, at least a portion of the resin tube having a continuous cylindrical tube wall being compressively deformable in a diametrical direction thereof, the device comprising:

a light source which supplies light into the tube from a light supply part on a surface of the tube;

a light receiving element which receives the light, which has been supplied and passed through the wall of the tube and the fluid inside the tube, at a light receiving part located on an opposite side in a diametrical direction of the tube relative to the light supply part, and outputs a signal indicating an intensity of the light;

light path distance setting means which sets a plurality of light path distances between the light supply part and the light receiving part by compressively deforming the portion of the resin tube having the continuous cylindrical tube wall while holding the tube; and fluid concentration output means which, from the light intensity at the light receiving part located at each of the plurality of light path distances, obtains a plurality of relational expressions, which indicate relation between the light intensity and the fluid concentration when the light from the light supply part is received by the light receiving part over each of the light path distances, based on the Beer-Lambert law, and obtains the fluid concentration from the light intensity at the light receiving part based on the relational expressions for the plurality of light path distances and outputs the fluid concentration.

2. The fluid concentration measuring device according to claim 1, wherein the light path distance setting means has a plurality of pairs of light supply part and light receiving part having different intervals therebetween, and changes the light path distance of at least one of the plurality of light path distances by selectively using a corresponding at least one of the pairs of light supply part and light receiving part.

3. The fluid concentration measuring device according to claim 1, wherein the light path distance setting means changes the light path distance of at least one of the plurality of light path distances between the light supply part and the light receiving part by varying the interval between the light supply part and the light receiving part.

4. The fluid concentration measuring device according to claim 2, wherein the light path distance setting means changes the light path distance of at least one of the plurality of light path distances between the light supply part and the light receiving part by varying the interval between the light supply part and the light receiving part.

5. The fluid concentration measuring device according to claim 1, wherein the fluid concentration output means uses a table, which is obtained and stored in advance and shows the relation between the light intensity and the fluid concentration at the light receiving part located at each of the plurality of light path distances, to obtain the fluid concentration from the light intensity at the light receiving part and output the fluid concentration.

6. The fluid concentration measuring device according to claim 2, wherein the fluid concentration output means uses a table, which is obtained and stored in advance and shows the relation between the light intensity and the fluid concentration at the light receiving part located at each of the plurality of light path distances, to obtain the fluid concentration from the light intensity at the light receiving part and output the fluid concentration.

7. The fluid concentration measuring device according to claim 3, wherein the fluid concentration output means uses a table, which is obtained and stored in advance and shows the relation between the light intensity and the fluid concentration at the light receiving part located at each of the plurality of light path distances, to obtain the fluid concentration from the light intensity at the light receiving part and output the fluid concentration.

8. The fluid concentration measuring device according to claim 4, wherein the fluid concentration output means uses a table, which is obtained and stored in advance and shows the relation between the light intensity and the fluid concentration at the light receiving part located at each of the plurality of light path distances, to obtain the fluid concentration from the light intensity at the light receiving part and output the fluid concentration.

9. A fluid concentration measuring device which measures concentration of a fluid flowing through a resin tube having a light-transmissive, a cylindrical tube wall of the resin tube being compressively deformable in a diametrical direction thereof, the device comprising:

a light source which supplies light into the tube from a light supply part on a surface of the tube;

a light receiving element which receives the light, which has been supplied and passed through the wall of the tube and the fluid inside the tube, at a light receiving part located on an opposite side in a diametrical direction of the tube relative to the light supply part, and outputs a signal indicating an intensity of the light;

light path distance setting means which sets a plurality of light path distances between the light supply part and the light receiving part by compressively deforming the cylindrical tube wall while holding the tube, wherein the light path distance setting means has a plurality of pairs of light supply part and light receiving part having different intervals therebetween, and changes the light path distance by selectively using the pairs of light supply part and light receiving part; and fluid concentration output means which, from the light intensity at the light receiving part located at each of the plurality of light path distances, obtains a plurality of relational expressions, which indicate relation between the light intensity and the fluid concentration when the light from the light supply part is received by the light receiving part over each of the light path distances, based on the Beer-Lambert law, and obtains the fluid concentration from the light intensity at the light receiving part based on the relational expressions for the plurality of light path distances and outputs the fluid concentration.

10. A fluid concentration measuring device which measures concentration of a fluid flowing through a resin tube having a light-transmissive, a cylindrical tube wall of the resin tube being compressively deformable in a diametrical direction thereof, the device comprising:

a light source which supplies light into the tube from a light supply part on a surface of the tube;

a light receiving element which receives the light, which has been supplied and passed through the wall of the tube and the fluid inside the tube, at a light receiving part located on an opposite side in a diametrical direction of the tube relative to the light supply part, and outputs a signal indicating an intensity of the light;

light path distance setting means which sets a plurality of light path distances between the light supply part and the light receiving part by compressively deforming the cylindrical tube wall while holding the tube, wherein the light path distance setting means changes the light path distance between the light supply part and the light receiving part by varying the interval between the light supply part and the light receiving part; and fluid concentration output means which, from the light intensity at the light receiving part located at each of the plurality of light path distances, obtains a plurality of relational expressions, which indicate relation between the light intensity and the fluid concentration when the light from the light supply part is received by the light receiving part over each of the light path distances, based on the Beer-Lambert law, and obtains the fluid concentration from the light intensity at the light receiving part based on the relational expressions for the plurality of light path distances and outputs the fluid concentration.

\* \* \* \* \*